United States Patent [19]

Binon

[11] Patent Number: 5,040,983

[45] Date of Patent: * Aug. 20, 1991

[54] TEMPORARY DENTAL COPING

[75] Inventor: Paul P. Binon, Roseville, Calif.

[73] Assignee: Implant Innovations, Inc., West Palm Beach, Fla.

[*] Notice: The portion of the term of this patent subsequent to Apr. 9, 2008 has been disclaimed.

[21] Appl. No.: 299,081

[22] Filed: Jan. 23, 1989

[51] Int. Cl.$^5$ ............................................... A61C 8/00
[52] U.S. Cl. .................................... 433/173; 433/174
[58] Field of Search ................. 433/173, 174, 175, 176

[56] References Cited

U.S. PATENT DOCUMENTS 4,824,372 4/1989 Jorneus et al. ...................... 433/174
4,854,872 8/1989 Detsch ................................ 433/173

FOREIGN PATENT DOCUMENTS 0288444 10/1988 European Pat. Off. ............ 433/173
0288445 10/1988 European Pat. Off. ............ 433/173
0288446 10/1988 European Pat. Off. ............ 433/173
0296513 12/1988 European Pat. Off. ............ 433/173

Primary Examiner—Robert P. Swiatek
Assistant Examiner—Nicholas D. Lucchesi
Attorney, Agent, or Firm—Alfred H. Rosen

[57] ABSTRACT

A dental coping in the form of an elongated tubular body has a base portion adapted at a first end of the body to mate with the gingival aspect of the patient's implant fixture, and a thin-walled tubular portion extending to the other end of the body supragingivally from the base portion when the base portion is so mated. The base portion is substantially rigid, having a thicker sidewall than the thin-walled tubular portion. A shoulder is provided within the base portion, for cooperating with a bolt to fasten the coping to the implant fixture. A flange extends radially from the coping, preferably from the rigid base portion, for fixing in place a temporary restoration formed around the coping. The fabrication and use of fixed provisional restorations in partially edentulous patients undergoing treatment with osseointegrated fixtures is described.

10 Claims, 1 Drawing Sheet

U.S. Patent     Aug. 20, 1991     5,040,983
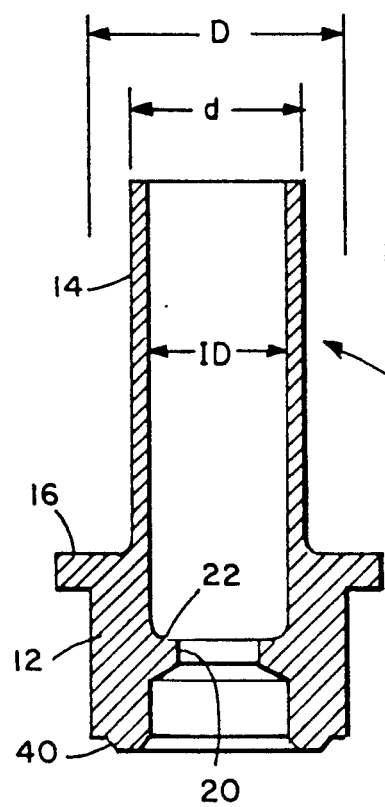
FIG. IA
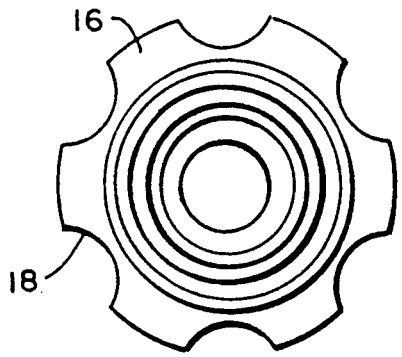
FIG. IB
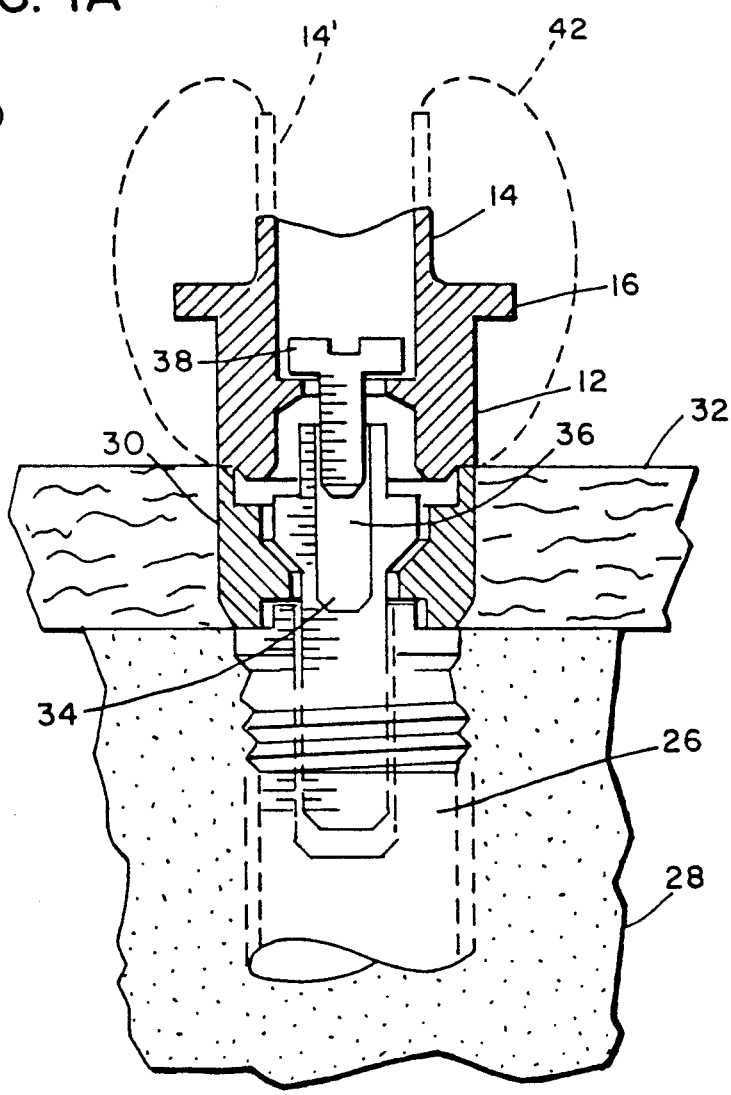
FIG. 2

TEMPORARY DENTAL COPING

This invention relates in general to restorative dentistry, and more particularly to methods and means for fixing a temporary dental restoration to an underlying support such as a dental implant fixture or the like.

While the field of restorative dentistry has made significant advances in the use of dental implants to support dental restorations intended to replace natural teeth, and intended for long-lasting use, very little attention, if any, has been given to providing a temporary restoration supported on a patient's implant fixture (or fixtures) for use while the permanent restoration is being prepared. Yet, dental restoration cases can take as long as one year, sometimes longer, to complete, from the time when the patient is prophylactically prepared to begin the series of treatments required in the fabrication of permanent dental restorations. During that rather extended time interval, a patient has need for inexpensive and reliable temporary dental restoration. Dental materials for use in chair-side preparation of temporary restorations are available for other, earlier, forms of restoration, on the patient's own prepared tooth-roots, for example, but prior to the present invention the field of restorative dentistry has lacked the ability to provide a temporary dental restoration supported on a dental implant fixture.

A widely-used form of dental implant fixture consists essentially of a generally cylindrical body implanted in a cylindrical bore made in the patient's jawbone, and having an internally-threaded cylindrical socket in which to fasten components used for attaching a permanent restoration to the implant fixture. The invention is illustrated and described with reference to implant fixtures taking that form. According to the invention, a dental coping in the form of an elongated tubular body has a base portion adapted at a first end of the body to mate with the gingival aspect of the patient's implant fixture, and a thin-walled tubular portion extending to the other end of the body supragingivally from the base portion when the base portion is so mated. The base portion is substantially rigid, having a thicker sidewall than the thin-walled tubular portion. A shoulder is provided within the base portion, for cooperating with a bolt to fasten the coping to the implant fixture. A flange extends radially from the coping, preferably from the rigid base portion, for fixing in place a temporary restoration formed around the coping. Such a restoration may be formed of the acrylic material that is currently in wide-spread use by prosthodontists for making temporary crowns and bridges.

Copings according to the invention may be made of a variety of materials which resist corrosion in the human mouth over a short term of one year, more or less. Among metals, palladium-silver alloy, stainless steel and aluminum are suitable materials. Among plastics materials, acrylics, similar to temporary crown and bridge materials, may be used. Other choices may be made. Another consideration is to choose a material having adequate resistance to deformation on loading, for the prosthesis being contemplated. In use, a temporary crown is fashioned around the coping, and the thin-walled tubular portion is cut to a suitable length for the crown. The bolt used to fasten the crown to the implant fixture is manipulated through the hole in the coping, and the hole is then filled with a temporary plug, to be drilled out later when access to the bolt is required to remove the temporary crown from the implant fixture. Such access may be required several times, to try-in a partially-prepared permanent restoration and, finally, to install the permanent restoration. Copings according to the invention are sufficiently rugged to permit such repeated installation and removal, while at the same time being inexpensive, and disposable, without damage to the underlying implant fixture, or to the temporary crown carried on it.

Other advantages and features of the invention will be apparent from the description of an exemplary embodiment of it which follows, with reference to the accompanying drawings, in which:

FIG. 1 is a longitudinal section (A) and a bottom view (B) of a coping according to the invention; and FIG. 2 shows a use of the coping in FIG. 1 to mount a temporary crown and to fix it removably to a dental implant fixture of a known kind.

In FIG. 1 a dental coping 10, generally tubular in shape, has a base portion 12 and a relatively thin-walled tubular portion 14 joined end-to-end. An annular retaining flange 16 extends radially outward from the coping in the region where the two portions join each other. This flange 16 terminates in a noncircular outer peripheral boundary 18 (FIG. 1B). The exterior diameter "D" of the base portion 12 is larger than the exterior diameter "d" of the thin-walled portion 14. The interior diameter "ID" of both portions is substantially the same. A radially-inwardly extending interior flange 20 located within the base portion 12 provides a shoulder 22 for a fastening means 38.

FIG. 2 shows a coping according to the invention fixed on a dental implant fixture 26 of a well-known type installed in a jawbone 28. A transmucosal component 30, penetrating the overlying gum tissue 32, is fixed to the implant fixture with a screw 34 the head portion of which has an internally-threaded socket 36 which receives the bolt 38 cooperating with the shoulder 22 to fix the coping 10 on the transmucosal component 30. The gingival end of the base portion 12 has an annular extension 40 which functions to mate with and center the coping coaxially on the transmucosal component 30.

The coping 10 is intended for use in removably fixing a temporary dental restoration on the support consisting of the dental implant fixture 26 and its transmucosal component 30, where a permanent prosthodontic restoration will eventually be fixed. A temporary dental restoration, outlined by a dashed line 42, is mounted on and around the coping, embracing the base portion 12 and the retaining flange 26, and extending supragingivally around the thin-walled portion 14. The thin-walled portion of the coping is cut or otherwise shortened to a length suitable for the crown being fashioned, as is indicated by dashed tubular lines 14'. The bolt 38 is installed through the tubular opening in the tubular portion 14, 14'. The latter opening may then be plugged with a temporary dental cement (not shown). The temporary dental restoration may be fashioned of any of the dental materials available for making temporary dental crowns and bridges (e.g: acrylics). The retaining flange 16 will keep it from moving axially along the coping 10, while the non-circular boundary 18 will restrict the temporary restoration from rotation around the axis of the coping. The peripheral boundary 18 of the retaining flange 16 can take shapes other than non-circular; for example, it can be round with saw-tooth serrations. For additional retention, holes (not shown) can be provided through the flange, into which the dental crown or bridge material can penetrate.

In addition to providing for the fabrication and use of fixed provisional restorations in partially edentulous patients undergoing treatment with osseointegrated fixtures, this invention serves as a diagnostic aid and an adjunct in tissue healing, and provides a back-up prosthesis for maintenance and a means for immediate verification by the patient of the benefits of tissue-integrated prosthesis.

I claim:

1. A dental coping for mounting a temporary dental restoration and fixing the same removably on a support such as a dental implant fixture or the like, comprising an elongated tubular body made of a material that resists corrosion in the human mouth around which to mount said restoration, said body having a substantially tubular rigid base portion adapted for mating at a first end of said body with said support, and means within said base portion providing a shoulder for cooperation with means to fasten said body to said support, extending supragingivally from said base portion when so fastened a relatively thin-walled tubular portion terminating at the other end of said body, and flange means located intermediate said ends of said body and extending therefrom radially outward from the exterior of said body, said flange means presenting a first annular side facing toward but spaced from said first end and a second annular side facing toward but spaced from said other end of said body, said flange means serving to retain said restoration when present mounted around said body so as to embrace both sides of said flange means.

2. A dental coping according to claim 1 in which said base portion has a larger exterior diameter than said thin-walled portion, and said flange means extends from said base portion near the juncture of said two portions.

3. A dental coping according to claim 2 in which the interior diameter of both of said portions is substantially the same.

4. A dental coping according to claim 3 in which said shoulder is provided on a surface of an interior annular flange extending radially inward from said base portion.

5. A dental coping according to claim 4 in which said interior flange is axially located between the ends of said base portion.

6. A dental coping according to claim 1 in which said flange means is an annular flange extending radially outward from said body and terminating in a non-circular peripheral boundary, for retaining a restoration, when present embracing it, against movement in the direction of the tubular axis as well as around said axis.

7. A dental coping according to claim 6 in which said exterior flange extends radially from said base portion near the juncture of said two portions.

8. A dental coping according to claim 1 in which said shoulder is provided on a surface of an interior annular flange extending radially inward from said base portion.

9. A dental coping according to claim 8 in which said interior flange is axially located between the ends of base portion.

10. A dental coping according to claim 1 in which said flange means is an annular flange extending radially outward from said body and terminating in an outer peripheral boundary comprising means for retaining a restoration, when present embracing it, against movement around the tubular axis of said body.

* * * * *